US006960699B2

(12) United States Patent
Tötsch et al.

(10) Patent No.: US 6,960,699 B2
(45) Date of Patent: Nov. 1, 2005

(54) METHOD FOR THE HYDROFORMYLATION OF OLEFINS

(75) Inventors: Walter Tötsch, Marl (DE); Detlef Arnoldi, Marl (DE); Alfred Kaizik, Marl (DE); Martin Trocha, Essen (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 10/506,603

(22) PCT Filed: Mar. 8, 2003

(86) PCT No.: PCT/EP03/02383

§ 371 (c)(1),
(2), (4) Date: Mar. 8, 2005

(87) PCT Pub. No.: WO03/078365

PCT Pub. Date: Sep. 25, 2003

(65) Prior Publication Data

US 2005/0171389 A1    Aug. 4, 2005

(30) Foreign Application Priority Data

Mar. 15, 2002  (DE) ............................ 102 11 652
Jun. 22, 2002  (DE) ............................ 102 27 995

(51) Int. Cl.⁷ ............................................ C07C 29/14
(52) U.S. Cl. ..................................... 568/882; 568/883
(58) Field of Search ................................. 568/882, 883

(56) References Cited

U.S. PATENT DOCUMENTS

| | | | |
|---|---|---|---|
| 2,816,933 A | 12/1957 | Mertzweiller | |
| 4,255,279 A * | 3/1981 | Spohn et al. | ................. 502/24 |
| 5,237,105 A * | 8/1993 | Summerlin | ................. 568/451 |
| 6,015,928 A | 1/2000 | Gubisch et al. | |
| 6,331,657 B1 | 12/2001 | Kaizik et al. | |
| 6,403,836 B2 | 6/2002 | Kaizik et al. | |
| 6,407,295 B1 | 6/2002 | Kaizik et al. | |
| 6,482,992 B2 | 11/2002 | Scholz et al. | |
| 6,720,457 B2 | 4/2004 | Drees et al. | |

FOREIGN PATENT DOCUMENTS

| | | |
|---|---|---|
| DE | 199 39 491 | 2/2001 |
| EP | 1 172 349 | 1/2002 |
| WO | 93 24437 | 12/1993 |

\* cited by examiner

*Primary Examiner*—Michael L. Shippen
(74) *Attorney, Agent, or Firm*—Oblon, Spivak, McClelland, Maier & Neustadt, P.C.

(57) ABSTRACT

The invention relates to a process for preparing alcohols by hydroformylation of olefins or olefin mixtures, separation from the catalyst and subsequent hydrogenation, with an extraction being carried out after removal of the catalyst and before the hydrogenation of the aldehydes.

11 Claims, 3 Drawing Sheets

METHOD FOR THE HYDROFORMYLATION OF OLEFINS

The invention relates to a process for preparing alcohols by hydroformylation of olefins or olefin mixtures in the presence of a cobalt catalyst, separation from the catalyst and subsequent hydrogenation, with an extraction to remove residue catalyst being carried out prior to the hydrogenation.

It is known that higher alcohols, in particular those having from 7 to 25 carbon atoms, can be prepared by catalytic hydroformylation (also referred as the oxo process) of the olefins having one less carbon atom and subsequent hydrogenation of the aldehydes formed. The alcohols can be used as solvents or as precursor for detergents or plasticizers.

A large number of processes for the hydroformylation of olefins are known in the literature.

EP 0 562 451 and EP 0 646 563 describe the hydroformylation of mixtures comprising 1- and 2-butene, with the 1-butene being reacted in a heterogeneous reaction, i.e. in a multiphase system, optionally with addition of a phase transferee or solubilizer, in the first stage and a homogeneously dissolved catalyst being used in the second stage. According to EP 0 562 451, rhodium catalysts are used in both stages, while in EP 0 646 563 rhodium catalysts are used in the first stage and cobalt catalysts are used in the second stage. According to EP 0 562 451, the olefin which has not been reacted in the first stage, predominantly 2-butene, is hydroformylated in a homogeneous phase and in the presence of rhodium catalyst in a second stage. In EP 0 646 563, this procedure is made more precise in that the olefins which have been not been reacted in the first stage leave the reactor in gaseous form together with carbon monoxide, hydrogen and butene formed by hydrogenation, i.e. an immediate separation of the olefins is carried out. The gas which has been separated off is, optionally after compression, passed to the second hydroformylation stage.

GB 1 387 657 describes a two-stage hydroformylation in which the reaction product of the first stage is discharged in gaseous form and, after the aldehydes or alcohols have been condensed out, the offgas from the first stage, which comprises unreacted olefins, is partly returned to the first stage and the remainder is passed to a second reactor.

A further variance of the two-stage hydroformylation is described in DE 32 32 557. In the first stage, the olefins are hydroformylated in the presence of a cobalt catalyst to conversions of 50 to 90%, the cobalt catalyst is separated off from the reaction mixture and the aldehydes formed together with the unreacted olefins are introduced into a second hydroformylation stage. The ligand-modified cobalt catalyst used here catalyzes not only the hydroformylation of the olefins but at the same time hydrogenation of the aldehydes to the alcohols.

DE 100 34 360.0 describes a process for the multistaged cobalt- or rhodium-catalyzed hydroformylation of olefins having from 6 to 24 carbon atoms to give alcohols and/or aldehydes, in which the olefins a) are hydroformylated to a conversion of from 20 to 98% in a hydroformylation step,
b) the catalyst is removed from the liquid reactor output obtained in this way,
c) the liquid hydroformylation mixture obtained in this way is separated into a low-boiling fraction comprising olefins and paraffins and a bottom fraction comprising aldehydes and/or alcohols,
d) the olefins present in the low-boiling fraction are reacted in further process stages comprising the process steps a, b and c, and the bottom fractions from the process step c) of all process stages are combined.

This process is preferably carried out so that the liquid reactor output from the hydroformylation step a) is a homogeneous liquid phase. The cobalt or rhodium-catalysts are preferably used in such a way that they are homogeneously dissolved in the liquid reactor output from the hydroformylation step a).

DE 198 42 368 A1 describes a process for preparing higher oxo alcohols from mixtures of isomeric olefins having from 5 to 24 carbon atoms by two-stage hydroformylation in the presence of a cobalt or rhodium catalyst at elevated temperature and superatmospheric pressure, in which the reaction mixture is selectively hydrogenated in the first hydroformylation stage, the hydrogenation mixture is separated by distillation into crude alcohol and low boilers consisting predominantly of olefins, these are fed to the second hydroformylation stage, the reaction mixture of the second hydroformylation stage is once again selectively hydrogenated, the hydrogenation mixture is separated by distillation into crude alcohol and low boilers, the crude alcohol is worked up by distillation to give pure alcohol and at least part of the low boilers are taken off to remove saturated hydrocarbons from the system.

The residue cobalt catalyst remaining in the organic phase generally amounts to less than 5 ppm of cobalt (calculated as metal). This residue cobalt can have adverse effects both on the hydrogenation and on the work-up by distillation as the operating time increases.

It has been found that the hydrogenation catalysts used are deactivated by the residue cobalt in the organic phase as the operating time increases. Particularly in prolonged operation, cobalt deposits have been observed on the catalyst surface.

Apart from catalyst deactivation, the cobalt deposits also adversely effect the hydrodynamics and the mass transfer and/or heat transport in the hydrogenation reactor.

EP 1 057 803 discloses a two-stage process for preparing alcohols from olefins or olefin mixtures. In the first reaction stage of this process, the feed olefin is hydroformylated to a conversion of from 50 to 90% in the presence of a cobalt catalyst. After the catalyst has been separated off, the unreacted olefins are separated from the reaction mixture by distillation and the olefins which have been separated off are reacted in the second hydroformylation reactor. The hydroformylation products from both stages can be hydrogenated to the corresponding alcohols. In both reaction stages, $Co_2(CO)_8$ or $HCo(CO)_4$ produced outside the hydroformylation reactors is used as catalyst. The cobalt catalyst is removed from the reaction mixture from the hydroformylation by extraction with a base before further processing.

In most of the cobalt-catalyzed hydroformylation processes known from the literature, the cobalt catalyst ($HCo(CO)_4$ or $Co_2(CO)_8$) is destroyed by oxidation after the hydroformylation step. This is generally carried out by reaction of the hydroformylation product mixture with air in the presence of an aqueous phase, so that the cobalt(II) salts produced in this way are extracted into the aqueous phase. The aqueous phase is separated off by, for example, decantation in a phase separation vessel or in other apparatuses suitable for this purpose. After the aqueous phase has been separated off, the organic phase is passed to a catalytic hydrogenation.

It was therefore an object of the present invention to reduce the cobalt content of the organic phase which is fed to the final hydrogenation in a process for the hydroformylation of olefins.

Surprisingly, the cobalt content of the aldehyde-containing fraction which is hydrogenated to the desired alcohol has been able to be reduced to low residue contents which cause virtually no interference by means of a simple extraction step using a water-containing liquid.

The present invention accordingly provides a process for preparing aliphatic alcohols having from 7 to 17 carbon atoms by means of one or more reaction stages which each comprise the steps a) cobalt-catalyzed hydroformylation of olefins having from 6 to 16 carbon atoms,
b) treatment of the hydroformylation mixture with oxygen-containing gases in the presence of acidic, aqueous cobalt (II) salt solutions,
c) separation of the mixture from b) into an aqueous phase comprising cobalt salts and an organic phase comprising the aliphatic aldehydes,
d) hydrogenation of the aldehyde-containing organic phase, wherein
e) the organic phase from c) is extracted with a water-containing liquid.

In one process variance, at least one further step f) in which the organic phase from b) is completely or partly separated by distillation into a low-boiling fraction comprising unreacted olefins and an aldehyde-containing bottom fraction is carried out, and the organic phase and/or the aldehyde-containing bottom fraction is extracted with a water-containing liquid in step e).

The process of the invention can comprise one or more stages which each comprise the steps a), b), c), d) and e) or the steps a), b), c) and e) with a joint process step d). Step f) may be carried out in each stage or jointly for all stages.

If the process of the invention is carried out in one stage, all or part of the organic phase separated off in step c) can be passed to either the process step d) or the process step f). Preference is given to passing on only part of the organic phase so as to create an outlet for the aliphatic compounds which would otherwise accumulate.

In these process variants, the process of the invention preferably comprises 2, 3 or 4 stages.

The process of the invention or any process stage and any process step can be carried out continuously or batchwise. Preference is given to carrying out all process steps continuously. A number of process variants are possible.

Variant 1:

In this process variant, at least two reaction stages are carried out, with the low-boiling fraction separated off in step f) being passed to step a) of the following reaction stage and the aldehyde-containing bottom fractions separated off in the steps f) of all reaction stages are hydrogenated in a joint step d). In this process variant, therefore, the steps a), b), c) and f) are carried out successively and only the hydrogenation of the aldehyde fraction d) is carried out jointly for all reaction stages.

Figure 1:
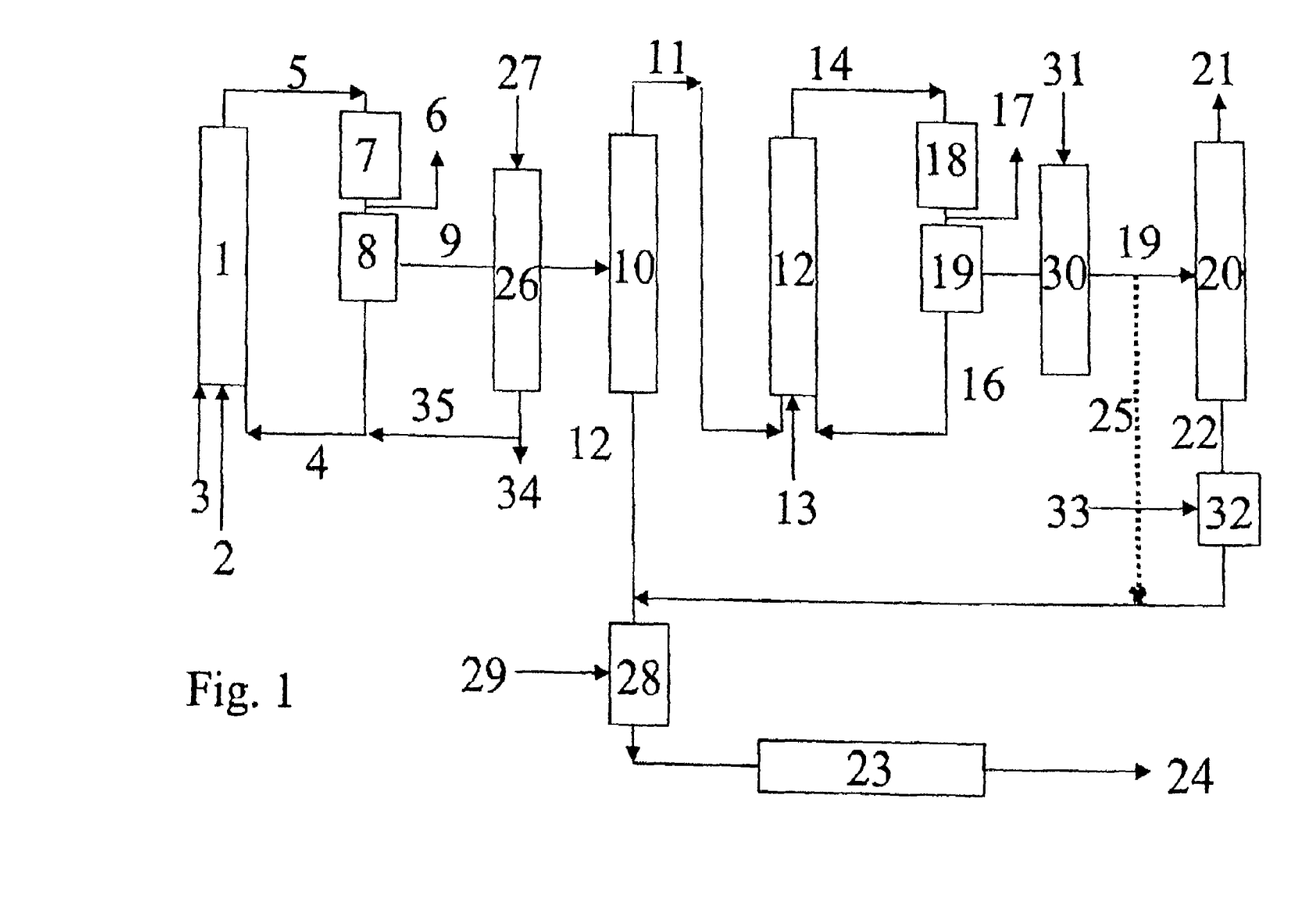

A block diagram of variant 1 of the process is shown in FIG. 1. The olefin mixture 3, the synthesis gas 2 (carbon monoxide and hydrogen) and an aqueous solution of a cobalt compound or cobalt catalyst and water are fed into the first hydroformylation reactor 1. The hydroformylation mixture 5 obtained in this way is depressurized, and the depressurized hydroformylation mixture is subjected to the decobalting 7 by means of aqueous, acidic cobalt(II) salt solution and air and is then freed of cobalt compounds 4 in the first catalyst removal 8. The gas from the depressurization, i.e. unconsumed synthesis gas, is taken off via line 6 prior to catalyst removal 8. The aqueous phase comprising cobalt salts is, if desired after bleeding off a small substream and after replacing it with fresh catalyst, returned to the first hydroformylation reactor 1. For the present purposes, the term catalyst also encompasses precursors of catalysts, e.g. cobalt(II) salt solutions. The organic phase 9 which has been freed of the catalyst is separated in a separation stage 10 into a hydrocarbon fraction 11 which consists predominantly of unreacted olefins and crude aldehyde 12. The low boilers 11, synthesis gas 13 and an aqueous solution of a cobalt compound or a preformed cobalt catalyst and water 16 are introduced into the second hydroformylation reactor 12. The hydroformylation mixture 14 from the second hydroformylation reactor 12 is again depressurized and the depressurization gas 17 is taken off after decobalting 18. The depressurized hydroformylation mixture 14 is subjected to the second decobalting stage 18 and then, in the second catalyst removal 19, freed of the catalyst which is once again, if desired after bleeding off a small substream and replacing with fresh catalyst, returned to the second hydroformylation reactor 12 (via 16). The decatalyzed hydroformylation mixture 19 can be separated in the separation stage 20 into a hydrocarbon fraction 21 consisting predominantly of saturated hydrocarbons and crude aldehyde 22. If desired, part of the hydrocarbon fraction 21 can be recirculated to the reactor 12 (a line not shown in FIG. 1).

In a further embodiment of this process variant, the decobalted hydroformylation mixture 19 is not separated in the separation stage 20 but is instead passed together with the crude aldehyde 12 from the first hydroformylation stage to the hydrogenation 23 (line 25). The crude aldehydes 12 and 22 or 12 and 25 are hydrogenated by means of hydrogen in the hydrogenation reactor 23 to give the crude alcohol 24 which can optionally be worked up in a distillation (not shown) to give pure alcohol.

The extraction according to the invention of the organic phases or the aldehyde-containing fractions can be carried out at one or more points in this process variant:

1. between the first catalyst removal (8) and the first distillation (10) in the extraction column 26;
2. after the first distillation (10) and the hydrogenation stage (23) in the extraction column (28);
3. between the second catalyst removal (19) and the second distillation (20) in the extraction reactor (30); and/or
4. after the second distillation (20) and the hydrogenation stage (23) in the extraction reactor (32).

The extractant is fed in via the lines (27), (29), (31) and/or (33).

The cobalt-containing extraction liquids obtained in the extraction procedure can be discharged (34) or, if appropriate after being concentrated, returned to the catalyst circuit (35). In FIG. 1, the further processing of the cobalt-containing extraction liquid is shown by way of example in the extraction stage 26. Analogous recirculation is also possible for the extraction stages 28, 30 and/or 32.

In this embodiment of the invention, each process stage has a hydroformylation step a), a decobalting step b), a catalyst removal step c) and a separation step f), with the proviso that the catalyst separated off in c) is recirculated either directly or after work-up to the hydroformylation step a) of the respective process stage.

If desired, this process variant can also be carried out with no separation step f) being present in the last process stage.

Variant 2

In this process variant, two reaction stages are carried out, with the low boilers separated off in step f) of the first reaction stage being passed to step a) of the second reaction stage and the organic output from the step c) of both stages being passed to step f) of the first reaction stage. Here, each reaction stage has a hydroformylation step a), a decobalting step b) and a catalyst removal step c), with the catalyst phase which has been separated off being recirculated to the respective hydroformylation step. The organic phase which has been separated off is separated in a joint separation step f) for both reaction stages into a low-boiling fraction and an aldehyde-containing bottom fraction. The low-boiling fraction obtained in this way is passed to the hydroformylation step a) of the second reaction stage, and the bottom fraction which has been separated off is passed to a joint hydrogenation step d).

Figure 2:
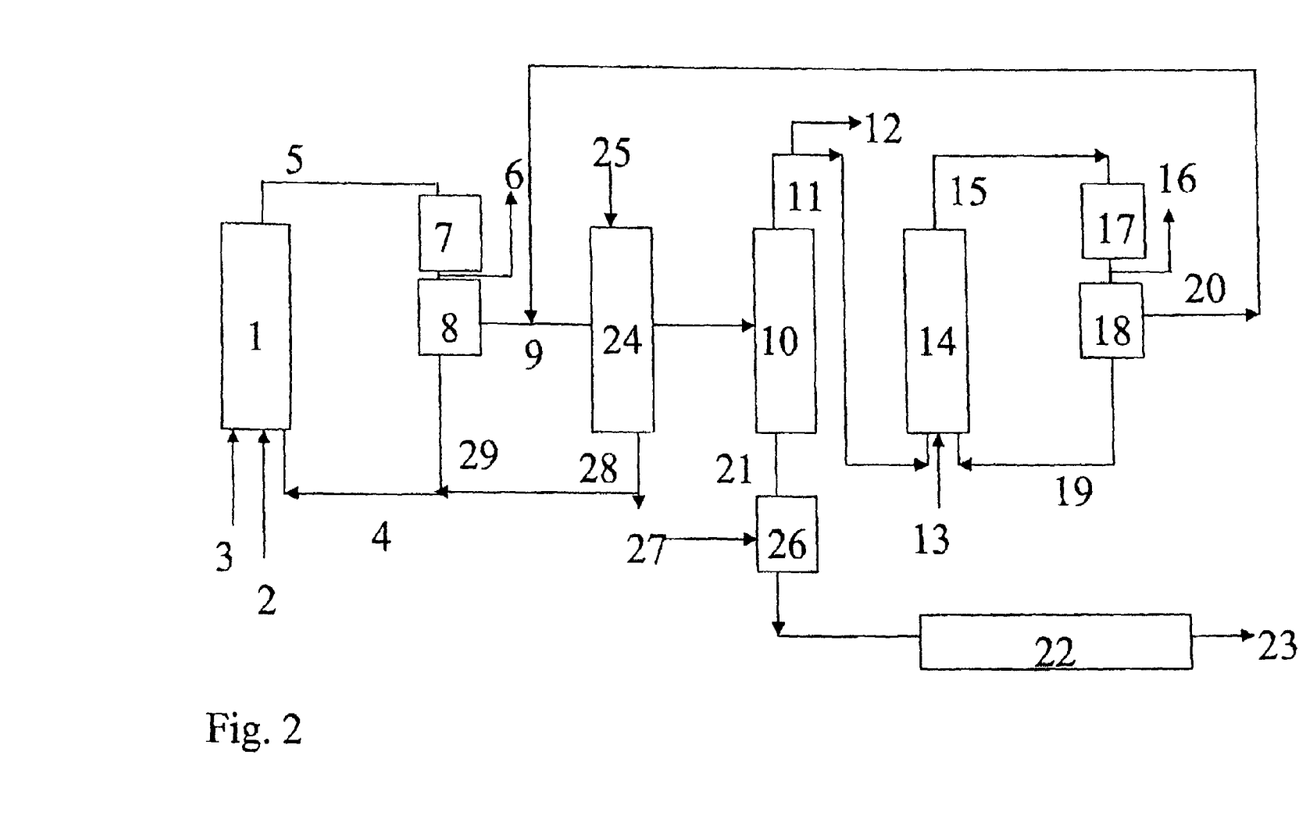

The block diagram of this process variant is shown in FIG. 2. The olefin mixture 3, the synthesis gas 2 (carbon monoxide and hydrogen) and an aqueous solution of a cobalt compound or cobalt catalyst together with water are fed into the first hydroformylation reactor 1. The hydroformylation mixture 5 obtained in this way is depressurized, and the depressurized hydroformylation mixture is subjected to decobalting 7 by means of aqueous, acidic cobalt(II) salt solution and air and then freed of cobalt compounds 4 in the first catalyst removal 8. The gas from the depressurization, i.e. unconsumed synthesis gas, is taken off via line 6 prior to the catalyst removal 8. The aqueous phase comprising cobalt salts is, if desired after bleeding off a small substream and replacing it with fresh catalyst, returned to the first hydroformylation reactor 1. The decobalted organic phase 9 is passed to the separation stage 10. There, it is, together with the decobalted hydroformylation mixture 20 from the second hydroformylation reactor 14, separated into a fraction 11 comprising unreacted olefins and inert paraffins and crude aldehyde 21. The hydrocarbon fraction 11 is, after bleeding off a substream 12 to remove saturated hydrocarbons (paraffins) and other common non olefinic compounds, fed together with synthesis gas 13 and an aqueous solution of a cobalt compound or a mixture of cobalt catalyst and water 19 into the second hydroformylation reactor 14. The hydroformylation mixture 15 obtained in this way is depressurized, the depressurization gas 16 is taken off after decobalting 17, and the depressurized hydroformylation mixture is, after decobalting 17, freed of the catalyst 19 in the second catalyst removal 18. The catalyst which has been separated off is, if desired after bleeding off a small substream and replacing it with fresh catalyst, returned to the second hydroformylation reactor 14. The decobalted second hydroformylation mixture 20 is fed together with the hydroformylation mixture 9 into, as mentioned above, the separation stage 10. The crude aldehyde 21 is hydrogenated by means of hydrogen in the hydrogenation unit 22 to give crude alcohol 23. This alcohol can be worked up in a distillation (not shown) to give the pure alcohol.

In this process variant, it is possible to carry out the additional extraction of reaction step e) between the first catalyst removal (8) and the separation by distillation (10) in the extractor (24) using the feed (25) and/or after the distillation stage (10) and before the hydrogenation stage (22) in the extractor (26) using the feed (27).

In this variant, too, the cobalt-containing extraction waters from the extraction stages can be either discharged (28) or returned to the catalyst circuit (29). FIG. 2 shows this by way of example for the extraction stage 24.

In this embodiment of the invention, each process stage has a hydroformylation step a), a decobalting stage b) and a catalyst removal step c), with the combined liquid hydroformylation mixtures being separated into a low-boiling fraction and a bottom fraction in a joint distillation step f), with the proviso that the catalyst separated off in steps b) and c) is recirculated directly or after the work-up to the hydroformylation step a) of the respective process stage.

Variant 3

In a further variant of the process of the invention, two reaction stages are carried out, with the low boilers separated off in step f) of the first reaction stage being passed to step a) of the second reaction stage and each of the steps b), c) and d) being carried out jointly for the two reaction stages. Here, the work-up of the product mixtures from the hydroformylation steps a) of the two reaction stages is carried out in joint steps b), c) and d).

Figure 3:
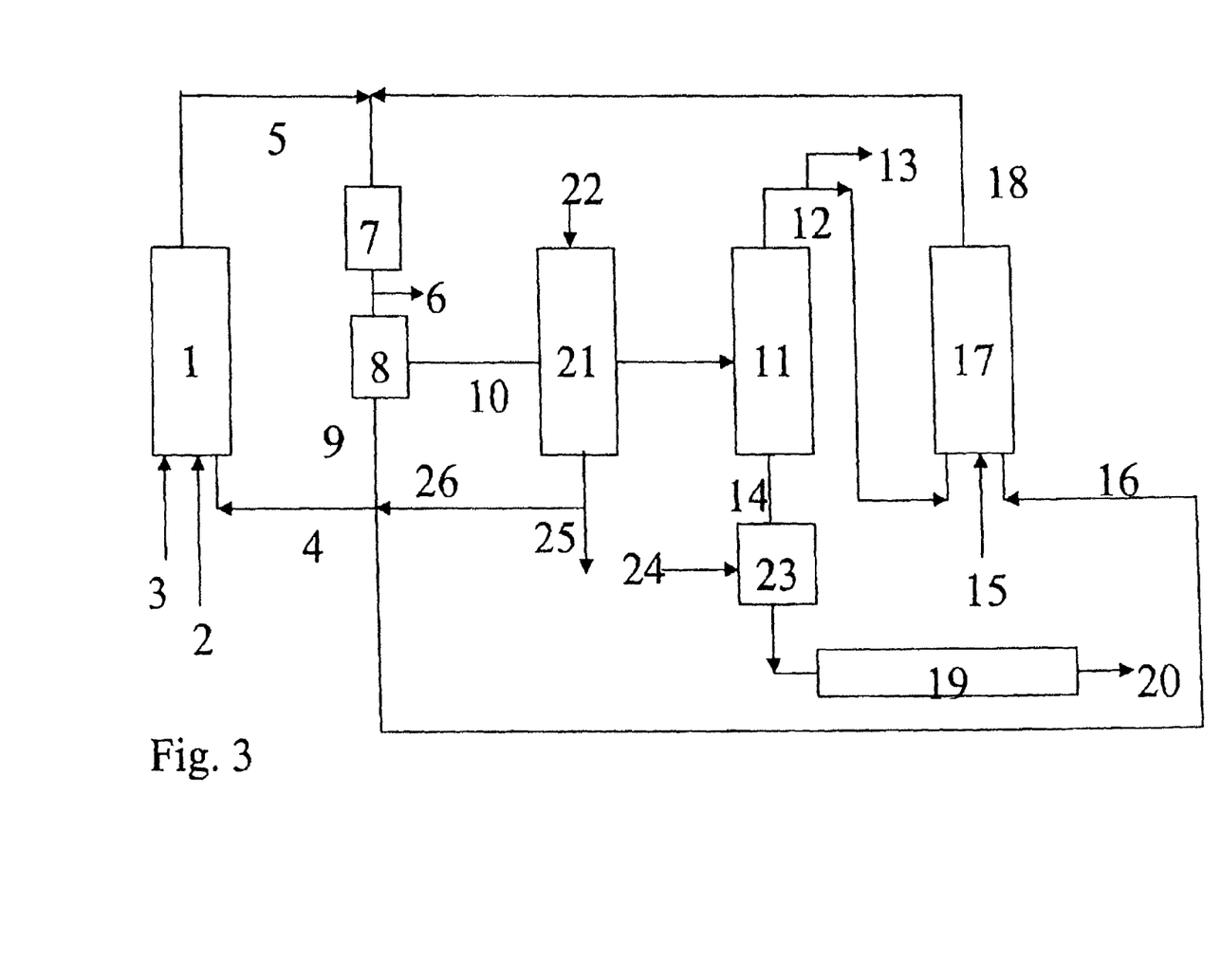

This variant of the process of the invention is shown in FIG. 3. The olefin mixture 3, the synthesis gas 2 (carbon monoxide and hydrogen) and an aqueous solution of a cobalt compound or a mixture of cobalt catalyst and substream 4 are fed into the first hydroformylation reactor 1. The hydroformylation mixture 5 obtained in this way is depressurized together with the hydroformylation mixture 18 from the second hydroformylation reactor 17 as combined hydroformylation outputs, and the depressurization gas 7 (unconsumed synthesis gas) is taken off after decobalting 7. After the decobalting stage 7, the organic phase is freed of the catalyst 9 in the catalyst separation 8. This gives a mixture 10 which comprises the aldehydes formed, alcohols and unreacted olefins. The catalyst 9 is, if desired after bleeding off a substream and replacing it with fresh catalyst, divided into the two substreams 4 and 16. Substream 4 is recirculated to the first hydroformylation reactor 1 and substream 16 is fed into the second hydroformylation reactor 17. The decobalted hydroformylation output 10 is separated in the separation stage 11 into the hydrocarbon fraction 12 and the crude aldehyde 14. The hydrocarbon fraction 12 comprising the unreacted olefins is, if desired after bleeding off a substream 13 to remove saturated hydrocarbons or other nonolefinic compounds, fed together with synthesis gas 15 and an aqueous solution of a cobalt compound or a mixture of cobalt catalyst and water 16 into the second hydroformylation reactor 17. The crude aldehyde 14 is hydrogenated by means of hydrogen in the hydrogenation unit 19 to give the crude alcohol 20. This can in turn be worked up in a distillation (not shown) to give pure alcohol.

In this process variant, the extraction e) can be carried out between the catalyst removal 8 and the work-up by distillation 11 in the reactor 21 using the feed 22, and/or between the work-up by distillation 11 and the hydrogenation stage 19 in the extraction reactor 23 using the water feed 24. Preference is given to the latter variant.

In variant 3, too, removal of saturated hydrocarbons can be carried out via a separate work-up of a substream of the hydroformylation mixture 18, for example by separating off the low boilers by distillation.

As in variants 1 and 2, the cobalt-containing extraction solution can be either discharged (25) or returned to the catalyst circuit (26).

In this embodiment of the process of the invention, the combined reactor outputs of all hydroformylation steps a) are subjected to only one decobalting stage b) and one catalyst removal step c) and one olefin removal step f), with the proviso that the catalyst separated off in the process steps b) and c) is divided either directly or after work-up and is recirculated to the hydroformylation step a) of the individual process stages.

The extraction e) can be carried out at various points in the process of the invention. In the following, the reaction steps a)–d) will firstly be described in more detail.

a) Hydroformylation Reaction

The reactors in which the hydroformylation is carried out can be identical or different in all process stages. Examples of types of reactor which can be used are bubble columns, loop reactors, jet nozzle reactors, stirred reactors and tube reactors, some of which can be cascaded and/or provided with internals.

The starting materials for the process of the invention are olefins or mixtures of olefins having from 6 to 16 carbon atoms, advantageously from 8 to 16 carbon atoms, in particular from 8 to 12 carbon atoms and terminal or internal C—C double bonds. The mixtures can consist of olefins having the same number of carbon atoms or similar (±2) or significantly different (>±2) numbers of carbon atoms. Examples of olefins which can be used as starting materials, either in pure form, as an isomer mixture or in a mixture with further olefins having a different number of carbon atoms, are: 1-, 2- or 3-hexene, 1-heptene, linear heptenes having an internal double bond (2-heptene, 3-heptene, etc.), mixtures of linear heptenes, 2- or 3-methyl-l-hexene, 1-octene, linear octenes having an internal double bond, mixtures of linear octenes, 2- or 3-methyl heptene, 1-nonene, linear nonenes having an internal double bond, mixtures of linear nonenes, 2- 3- or 4-methyl octenes, 1-, 2-, 3-, 4- or 5-decene, 2-ethyl-1-octene, 1-dodecene, linear dodecenes having an internal double bond, mixtures of linear dodecenes, 1-tetradecene, linear tetradecenes having an internal double bond, mixtures of linear tetradecenes, 1-hexadecene, linear hexadecene having an internal double bond, mixtures of linear hexadecenes. Further suitable starting materials are, inter alia, the mixture of isomeric hexene formed in the dimerization of propene (dipropene), the mixture of isomeric octene formed in the dimerization of butenes (dibutene), the mixture of isomeric nonene formed in the trimerization of propene (tripropene), the mixture of isomeric dodecene formed in the tetramerization of propene or the trimerization of butenes (tetrapropene or tributene), the hexadecene mixture formed in the tetramerization of butenes (tetrabutene) and also olefin mixtures prepared by cooligomerization of olefins having different numbers of carbon atoms (preferably from 2 to 4), if desired after separation into fractions having an identical or different (±2) number of carbon atoms by distillation. It is also possible to use olefins or olefin mixtures which have been produced by the Fischer-Tropsch synthesis. Furthermore, olefins which have been prepared by olefin metathesis or other industrial processes can also be used. Preferred starting materials are mixtures of isomeric octene, nonene, dodecene or hexadecene, i.e. oligomers of lower olefins such as n-butene, isobutene or propene. Other starting materials which are likewise well suited are oligomers of $C_5$-olefins.

For the oligomerization of butenes to give mixtures consisting essentially of $C_8$-olefins, there are in principal three process variants. Oligomerization in the presence of acidic catalysts, which in industrial practice may be, for example, zeolites or phosphoric acid on supports, have been known for a long time. This gives isomer mixtures of branched olefins, essentially dimethylhexenes (WO 92/13818). Another process which is likewise practiced worldwide is oligomerization using soluble Ni complexes, known as the DIMERSOL process (see J. Schulze, M. Homann, "$C_4$-Hydrocarbons and Derivatives", Springer-Verlag, Berlin, Heidelberg 1989, p. 69 and B. CORNILS, W. A. HERRMANN, "Applied Homogeneous Catalysis with Organometallic Compounds", Vol. 1 and 2, VCH, Weinheim, N.Y. 1996). The third process variant is oligomerization over fixed-bed nickel catalysts; this process is the OCTOL process (Hydrocarbon Process., Int. Ed. (1986) 65 (2. Sect. 1) Pages 31–33).

For the preparation according to the invention of a $C_9$-alcohol mixture which is suitable, in particular, for the preparation of plasticizers, preference is given to using a $C_8$-olefin mixture which has been obtained from linear butenes by the OCTOL process as starting material.

In the process of the invention, the hydroformylation of the olefins is carried out in the presence of cobalt catalysts, preferably unmodified catalysts such as $HCo(CO)_4$ and/or $Co_2(CO)_4$, and of water. Either preformed catalyst or a catalyst precursor, e.g. a cobalt compound, from which the actual catalyst is formed in the reactor can be fed into the hydroformylation reactor.

If the finished, active catalyst (e.g. $HCo(CO)_4$ and/or $Co_2(CO)_4$) is used, water, olefin, catalyst and synthesis gas are fed to the reactor. Water can have been dispersed in the olefin upstream of the reactor, for example by use of a static mixer, however, it is also possible for all compounds to be mixed only in the reactor.

The amount of water in the hydroformylation reactor can be varied within wide limits. Water can be homogeneously dissolved or additionally dispersed in the liquid hydroformylation output by setting the ratio of water and olefin and the reaction parameters, for example temperature.

In the process of the invention, the formation of the catalyst ($HCo(CO)_4$ and/or $Co_2(CO)_4$) in the hydroformylation reactor is preferred. For example, such a process is described in DE 196 54 340. According to this process, the starting materials, e.g. the cobalt salt solution, the organic phase and the synthesis gas, are introduced simultaneously, preferably with the aid of a mixing nozzle, in cocurrent into the reactor from the bottom.

As cobalt compounds, preference is given to using cobalt salts such as formates, acetates or salts of carboxylic acids which are soluble in water. It has been found to be particularly useful to use cobalt-acetate as an aqueous solution having a cobalt content of from 0.5 to 3% by mass, preferably from 0.8 to 1.8% by mass, calculated as metal. A further preferred starting solution for formation of the catalyst is the aqueous cobalt salt solution which is obtained in separation step c).

The amount of water desired in the hydroformylation reactor can be introduced via the cobalt salt solution whose concentration can be varied within a wide range. However, it is also possible to feed further water into the reactor in addition to the cobalt salt solution.

In the cobalt-catalyst process, the introduction of the starting materials into the reactor is of particular importance. The introduction facility has to ensure a good mixing of the phases and generation of a very high mass transfer area between the phases. Furthermore, it is advantageous to divide the interior of the hydroformylation reactors by installation of from 1 to 10, preferably from 2 to 4, perforated plates positioned perpendicular to the flow direction of the reactant stream and product stream. This cascading of the reactor greatly reduces backmixing compared to a simple bubble column and the flow behavior approaches that of a tube reactor. This process engineering measure results in improvements in both the yield and the selectivity of the hydroformylation.

Precise details of hydroformylation steps may be found in DE 199 39 491 A1 and DE 101 35 906.3.

According to DE 199 39 491, a substream of the liquid mixed phase (aqueous cobalt salt solution/organic phase) is taken off from the lower part of the reactor and is fed back in at a point higher up on the reactor. According to DE 101 35 906.3, the level of an aqueous bottom phase in which the concentration of cobalt compounds (calculated as metallic cobalt) is in the range from 0.4 to 1.7% by mass is kept constant in the hydroformylation reactor.

The hydroformylation steps can be carried out under identical or different conditions; preference is given to temperatures of from 100 to 250° C. and pressures of from 100 to 400 bar. Temperatures of from 140 to 210° C. and synthesis gas pressures of from 200 to 300 bar have been found to be particularly useful. The volume ratio of carbon monoxide to hydrogen in the synthesis gas is generally from 2:1 to 1:2, in particular 1:1.5. The synthesis gas is advantageously used in excess, for example up to three times the stoichiometric amount.

In multistage process variants, the hydroformylation is advantageously carried out at temperatures of from 140 to 195° C., preferably from 160 to 185° C., in the first process stage in which the more reactive olefins are reacted. In this process stage, olefin conversions of from 20 to 95%, preferably from 50 to 80%, are sought.

In the liquid hydroformylation output, the concentration of cobalt compounds (calculated as metallic cobalt) is from 0.01 to 0.5% by mass, in particular from 0.02 to 0.08% by mass (based on the sum of organic and aqueous phases).

Due to the different possible ways of adding water, the water content in the input into the hydroformylation reactor can be determined only with difficulty. For this reason, the following discussion will refer only to the output from the reactor, with the water content in the output from the reactor being virtually the same as the water content of the liquid phase during the reaction.

The water concentrations in the liquid hydroformylation outputs can be from 0.1 to 10% by mass, in particular from 0.5 to 5% by mass. The water content of the hydroformylation outputs of the individual stages are identical or different. The water is preferably homogeneously dissolved in the liquid hydroformylation outputs.

b) Catalyst removal

The product mixtures leaving the hydroformylation reactors are depressurized to from 10 to 15 bar and passed to the respective separation stage c) including decobalting b). In the decobalting step b), the product mixture (liquid organic phase) from the hydroformylation reaction a) is reacted with oxygen-containing gases, in particular air or oxygen, in the presence of acidic, aqueous cobalt(II) salt solutions ("process water") at temperatures of from 90 to 160° C. and are thus freed of cobalt carbonyl complexes by oxidation. The hydroformylation-active cobalt carbonyl complexes are thus destroyed to form cobalt(II) salts. Decobalting processes are well known and are comprehensively described in the literature, e.g. by J. FALBE, in "New Syntheses with Carbon Monoxide", Springer Verlag (1980), Berlin, Heidelberg, N.Y., page 158 ff).

The solution used has a pH of from 1.5 to 4.5 and a cobalt content as in the hydroformylation step, preferably from 0.8 to 2.0% by mass.

The decobalting b) is preferably carried out in a pressure vessel packed with packing elements, e.g. Raschig rings, in which a very high mass transfer area between the phases is generated. The virtually cobalt-free organic product phase is separated from the aqueous phase in a downstream separation vessel, i.e. the actual separation stage c). The aqueous phase, viz. "the process water", in which the cobalt which has been back-extracted and recovered from the organic phase and is present in the form of cobalt-acetate/formate is recirculated in its entirety or after bleeding off a small proportion to the oxo reactor of the respective process stage and is preferably used as starting material for the in-situ formation of the cobalt catalyst complexes.

If desired, part of the excess formic acid can be removed prior to the recirculation of the process water to the hydroformylation reactor. This can be carried out, for example, by distillation. Another possibility is to decompose part of the formic acid, for example, catalytically as described in DE 100 09 207. Furthermore, it is possible to prepare the actual hydroformylation catalyst ($Co_2(CO)_8$ and/or $HCo(CO)_4$) from the cobalt salt solution obtained in decobalting by precarbonylization and recirculated to the hydroformylation reactor.

c) Separation by Distillation

The organic reaction output obtained after the hydroformylation step and decobalting comprises unreacted olefins, aldehydes, alcohols, formic esters and high boilers and also traces of cobalt compounds. This output is passed to a fractionization (step f) in which the low boilers, preferably the unreacted olefins, are separated off from the products of value (aldehyde, alcohol, formates).

The olefins can be separated off from the hydroformylation products by, for example, distillation or steam distillation.

The low-boiling fraction (top fraction) comprises the unreacted olefins, the paraffins formed by hydrogenation of olefins, water and possibly small amounts of products of value. It is passed to the hydroformylation step of the next reaction stage or, if appropriate, the last reaction stage. If desired, the water is separated off, e.g. in a settler, and returned to the decobalting stages or the extraction stages.

d) Hydrogenation

The fractions comprising the hydroformylation products which are obtained from each hydroformylation stage after the unreacted olefins have been separated off can be hydrogenated separately or jointly (step d).

The decobalted hydroformylation mixture from the last stage can, if desired, be hydrogenated without the olefins being separated off. In this process variant, step f) is a method, at least in the last stage.

The hydrogenation can be carried out using, for example, copper, nickel, copper/nickel, copper/chromium, copper/chromium/nickel, zinc/chromium or nickel/molybdenum catalysts. The catalysts can be unsupported or the hydrogenation-active materials or their precursors can have been applied to supports such as aluminum oxide or silicon dioxide.

Preferred catalysts over which the hydroformylation mixtures are hydrogenated comprise from 0.3 to 15% by mass of copper and from 0.3 to 15% by mass of nickel and also, as activators, from 0.05 to 3.5% by mass of chromium and advantageously from 0.01 to 1.6% by mass, preferably from 0.02 to 1.2% by mass, of an alkali metal component on a support material, preferably aluminum oxide and silicon dioxide. The percentages are based on the not yet reduced catalyst. The alkali metal component is optional.

The catalysts are advantageously used in a form in which they offer a low flow resistance, e.g. in the form of granules, pellets or shaped bodies such as tablets, cylinders, extruded rods or rings. They are advantageously activated, e.g. by heating in a stream of hydrogen, before use.

The hydrogenation, preferably a liquid-phase hydrogenation, is generally carried out under a total pressure of from 5 to 100 bar, in particular from 15 to 50 bar. A hydrogenation in the gas phase can also be carried out at lower pressures, with a correspondingly large gas volume. If a polarity of hydrogenation reactors are used, the total pressures in the individual reactors can be identical or different within the above mentioned pressure limits.

The reaction temperatures both in liquid-phase or gas-phase hydrogenation are generally from 120 to 220° C., in particular from 140 to 180° C. Examples of such hydrogenations are described in the patent applications DE 198 42 369 and DE 198 42 370.

In the process of the invention, the hydrogenation is optionally carried out in the presence of water. The water required can be present in the feed to the reactor. However, it is also possible for water to be fed into the hydrogenation apparatus at any point. In the case of gas-phase hydrogenation, water is advantageously introduced in the form of water vapor. A preferred hydrogenation process is liquid-phase hydrogenation with addition of water, as described, for example, in DE 100 62 448.0.

The hydrogenation is preferably carried out at a water content of from 0.05 to 10% by mass, in particular from 0.5 to 5% by mass, very particularly preferably from 1 to 2.5% by mass. The water content is determined in the output from the hydrogenation.

e) Extraction

To remove traces of cobalt compounds, it is advantageous to subject the streams fed to the hydrogenation, i.e. the organic phases from the separation step c) or the aldehyde-containing bottom fractions from step f), to one or more extractions with a water-containing liquid, either separately or together.

The extractions e) can be carried out before and/or after the separation(s) by distillation f). It is advantageous to carry out only one extraction directly upstream of the hydrogenation stage d).

The residue cobalt contents of the organic phase are usually from 1 to 5 ppm of cobalt. In the case of an operational malfunction, e.g. a suboptimum phase separation, the residue amounts of cobalt in the organic phase can also become considerably higher.

As a result of the extraction according to the invention, the residue content of cobalt compounds is removed from the organic phases to such an extent that their content of cobalt compounds (calculated as cobalt) is reduced to below 0.5 ppm by mass, in particular below 0.2 ppm by mass, very particularly preferably below 0.1 ppm by mass. As a result, the specific consumption of cobalt compounds in the overall process can be reduced and the deactivation of the hydrogenation catalyst caused by deposits of cobalt or cobalt compounds can be decreased, so that longer operating lives of the catalysts are achieved.

Without the additional extraction step according to the invention, the typical operating lives of the catalysts are about 2 to 3 years. These operating lives can be reduced to about half a year in the event of increased residual cobalt contents, e.g. due to operational malfunctions.

On the basis of experience to date, the operating life of the catalyst can be increased significantly, i.e. at least double, by means of the extraction according to the invention of the residue cobalt.

The extraction of the cobalt compounds from the aldehyde-containing mixtures which are passed to the hydrogenation can be carried out using the extraction apparatuses known to those skilled in the art, for example simple extraction columns, sieve tray columns, packed columns or columns having moving internals. Examples of extraction apparatuses having moving internals are, inter alia, the rotary disk extractor and the disk column. A further apparatus which is used, in particular, in the case of high flow rates in the extraction is the mixer-settler extractor. It is also possible for two or more extractors of the same type or different types to be combined with one another.

In the process of the invention, the extraction of the cobalt compounds is preferably carried out as a countercurrent extraction. In this case, the extracter uses preferably a sieve tray column or a packed column, very particularly preferably a sieve tray column. The extraction medium (acceptor phase) is, as the heavier phase, fed in in the vicinity of the upper end of the column and the cobalt-containing organic aldehyde-containing phase (donor phase) is fed in as the lightener phase in the vicinity of the lower end of the column.

The acceptor phase is preferably passed through the extraction column in a single pass or with recirculation (circulation mode). The cobalt concentration (calculated as cobalt) in the extract (acceptor phase leaving the column) is below 2% by mass, in particular below 1% by mass, very particularly preferably below 0.5% by mass.

In the circulation mode, e.g. in the case of mixture-settler extraction, the cobalt concentrations of the acceptor phase are accordingly limited so that the abovementioned cobalt values are not exceeded in the extract.

The throughput ratio (mass/mass) of organic phase to free aqueous phase is from 200/1 to 5/1, preferably from 100/1 to 25/1. The extraction column is preferably operated so that the organic phase is the disperse phase. For this purpose, it can be advantageous to use specific inlet devices which cause the organic phase to be introduced into the extraction column in the form of small droplets.

The extraction is carried out at temperatures of from 10 to 180° C. in particular from 15 to 110° C., very particularly preferably from 40 to 90° C. At relatively high temperatures (about 100° C.), extraction is carried out under superatmospheric pressure so that both phases, in particular the water, are present in liquid form.

Apart from (pure) water as extractant, it is also possible to use aqueous solutions or mixtures with water, e.g. water/acid mixtures, preferably with mineral acids or carboxylic acids such as formic acid/water or acetic acid/water mixtures, in particular aqueous formic acid mixtures, as water-containing liquid for the extraction of the cobalt compounds. The acid concentration of the aqueous solutions is from 0.1 to 5% by mass, in particular from 0.5 to 1.5% by mass.

To avoid losses of aldehydes as a result of oxidation, the extraction is preferably carried out in the absence of oxygen.

The pH of the extractant is preferably $\leq 7$. It is likewise possible to use a mixture or a solution of water and an organic solvent, in particular the alcohol to be prepared.

The extraction e) can, as shown in the variants 1–3, be carried out at various points in the process. The extraction e) is preferably carried out once in each process stage or after the last stage, either before or after the separation by distillation f), very particularly preferably directly before the hydrogenation d).

The processes in which the olefin-containing outputs from the separation by distillation are selectively hydrogenated or dehydrogenated are also possible. Here too, the distillation can be preceded by an extraction stage e).

The extracts laden with cobalt compounds can be recirculated to suitable points of the process. For example, the extracts can be fed into one or more decobalting stages. Another possibility is to introduce the extracts into one or more hydroformylation reactors. Furthermore, the extracts can be introduced both into one or more decobalting stages and into one or more hydroformylation reactors. As an alternative, the extracts can be recirculated to the separation stages c).

The recirculation of the extracts enables amounts of cobalt and water which have been discharged from preceding stages together with the organic phases to be replaced. If the extracts contain more water than is consumed in the preceding stages, the extracts can be concentrated, for example by distilling off water, before they are recirculated.

The aldehyde-containing fractions which have been freed of traces of cobalt compounds are finally passed to one or more hydrogenation stages.

The hydrogenation product or products is/are worked up in one or more distillations to give the pure alcohol. In the case of high-boiling alcohols, the distillation is preferably carried out under reduced pressure.

The alcohols prepared by the process of the invention can, for example, be used as solvents or as precursors for plasticizers, e.g. phthalic esters or detergents.

The following example illustrates the invention without restricting its scope which is defined by the description and the claims.

EXAMPLES

Extraction of Cobalt by Means of Water in a Pilot Plant Extractor

As starting material for the extraction experiments, use was made of a cobalt-containing hydroformylation mixture from the cobalt-catalyzed hydroformylation of dibutene having a residue cobalt content of 5 ppm. The hydroformylation mixture comprised 6.5% by weight of C8-hydrocarbons, 35.6% by weight of C9-aldehydes, 49.7% of C9-alcholos, 3.5% by weight of isononyl formate and 4.5% by weight of high boilers.

In a pilot plant extractor made of stainless steel (length: 8000 mm, diameter: 50 mm) and having 20 sieve trays, 50 kg/h of the hydroformylation mixture (organic phase) were fed into the bottom of the extractor. At the top of the extractor, 0.5 kg/h of water as extractant was introduced in countercurrent to the organic phase.

The extraction experiments were carried out at a temperature of 85° C. and a pressure of 5 bar.

After steady-state operation had been established, the aqueous phase in the bottom of the extractor and the organic phase at the top of the reactor were analyzed to determine their cobalt contents.

Under the conditions selected, cobalt contents of 492 ppm (±10 ppm) were determined in the aqueous phase. The organic phase leaving the extractor contained, on average, 0.075 ppm (±0.005 ppm) of cobalt. On the basis of this result, the residue cobalt contents in the organic phase could be reduced by about 98% by countercurrent extraction with water.

What is claimed is:

1. A process for preparing aliphatic alcohols having from 7 to 17 carbon atoms, the process comprising one or more reaction stages which each comprise
   a) hydroformylating olefins having from 6 to 16 carbon atoms in the presence of a catalyst which comprises cobalt to obtain a hydroformylation mixture,
   b) treating the hydroformylation mixture with at least one gas which comprises oxygen in the presence of acidic, aqueous cobalt(II) salt solutions to obtain a second mixture,
   c) separating the second mixture from said treating b) into an aqueous phase comprising cobalt salts and an organic phase comprising the aliphatic aldehydes,
   e) extracting the organic phase from said separating c) with a liquid which comprises water
   d) hydrogenating the organic phase which comprises the aliphatic aldehydes.

2. The process as claimed in claim 1, further comprising
   f) separating all or part of the second mixture from said treating b) by distillation into a low-boiling fraction comprising unreacted olefins and a bottom fraction comprising the aldehyde,
   wherein, in said extracting e), the organic phase from said separating c) and/or the bottom fraction comprising the aldehyde from said separating f) is extracted with a liquid comprising water.

3. The process as claimed in claim 1, wherein said extracting e) is carried out using pure water.

4. The process as claimed in claim 1, wherein said extracting e) is carried out using an aqueous solution or a mixture of water with a mineral acid, a carboxylic acid and/or an organic solvent.

5. The process as claimed in claim 1, wherein the pH of the liquid comprising water is less than or equal to 7.

6. The process as claimed in claim 1, wherein the process comprises at least two reaction stages and all or part of the organic phase separated off in said separating c) is passed to said hydroformylating a) of the next reaction stage.

7. The process as claimed in claim 2, wherein all or part of the low-boiling fraction separated off in in said separating f) is returned to said hydroformylating a).

8. The process as claimed in claim 2, wherein the process comprises at least two reaction stages and the low-boiling fraction separated off in said separating f) is passed to said hydroformylating a) of the next reaction stage.

9. The process as claimed in claim 2, wherein the process comprises at least two reaction stages and the low-boiling fraction separated off in said separating f) is passed to said hydroformylating a) of the next reaction stage and the bottom fractions separated off in said separating f) of all reaction stages are hydrogenated in a joint said hydrogenating d).

10. The process as claimed in claim 2, wherein the process comprises two reaction stages and the low boiling fraction separated off in said separating f) of the first reaction stage is passed to said hydroformylating a) of the second reaction stage and the organic phase from said treating b) of both stages is passed to said separating c) of the first reaction stage.

11. The process as claimed in claim 2, wherein the process comprises two reaction stages and the low boiling fraction separated off in said separating f) of the first reaction stage is passed to said hydroformylating a) of the second reaction stage and said treating b), said separating c) and said hydrogenating d) are each carried out jointly for the two reaction stages.

* * * * *